United States Patent

Yoshida et al.

[11] Patent Number: 5,315,022

[45] Date of Patent: * May 24, 1994

[54] SILICONE TYPE CINNAMIC ACID DERIVATIVE, PREPARATION METHOD THEREOF, UV-RAY ABSORBER, AND EXTERNAL SKIN TREATMENT AGENT

[75] Inventors: Masashi Yoshida; Kenichi Umishio; Keiichi Uehara; Tomiyuki Nanba, all of Yokohama, Japan

[73] Assignee: Shiseido Company Ltd., Tokyo, Japan

[*] Notice: The portion of the term of this patent subsequent to Mar. 3, 2009 has been disclaimed.

[21] Appl. No.: 676,127

[22] Filed: Mar. 27, 1991

Related U.S. Application Data

[63] Continuation-in-part of Ser. No. 376,321, Jul. 6, 1989, Pat. No. 5,093,511.

[30] Foreign Application Priority Data

Jul. 8, 1988 [JP] Japan ................. 63-168838
Jul. 22, 1988 [JP] Japan ................. 63-181500
Mar. 31, 1990 [JP] Japan ................. 2-86440

[51] Int. Cl.$^5$ .............................. C07F 7/08
[52] U.S. Cl. ..................... 556/437; 556/440
[58] Field of Search ................. 556/440, 437

[56] References Cited

U.S. PATENT DOCUMENTS

| | | | |
|---|---|---|---|
| 2,732,391 | 1/1956 | Noll | 556/440 |
| 2,770,633 | 11/1956 | Sommer | 556/440 |
| 2,783,263 | 2/1957 | Merker | 556/440 |
| 2,872,434 | 2/1959 | Barnes | 556/440 X |
| 4,545,980 | 10/1985 | Hill | 556/440 X |
| 4,562,278 | 12/1985 | Hill | 556/418 |

FOREIGN PATENT DOCUMENTS 0138321 4/1985 European Pat. Off. .

*Primary Examiner*—Paul F. Shaver
*Attorney, Agent, or Firm*—Sprung Horn Kramer & Woods

[57] ABSTRACT

A silicone type cinnamic acid derivative which is a siloxane having at least one unit represented by the formula (I):

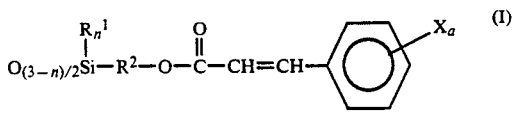

and having the other units which may exist in the siloxane being represented by the formula:

$$O_{(4-m)/2}SiR^3_m$$

wherein $R^1$ represents an alkyl group having 1 to 4 carbon atoms, a phenyl group, or a trimethylsiloxy group, $R^2$ is a divalent hydrocarbon group having at least two carbon atoms, which may include a heteroatom, O, X is an alkoxy group, n is an integer of 0 to 3, a is an integer of 2 or 3, $R^3$ is an alkyl group having 1 to 4 carbon atoms, a phenyl group, or a trimethylsiloxy group, and m is an integer of 0 to 3.

2 Claims, 3 Drawing Sheets

SILICONE TYPE CINNAMIC ACID DERIVATIVE, PREPARATION METHOD THEREOF, UV-RAY ABSORBER, AND EXTERNAL SKIN TREATMENT AGENT

CROSS-REFERENCE TO RELATED APPLICATION

This application is a continuations-in-part of Ser. No. 376,321, filed Jul. 6, 1989 now U.S. Pat. No. 5,093,511.

BACKGROUND OF THE INVENTION

1. Field of the Invention

The present invention relates to a novel silicone type cinnamic acid derivative and a method of preparing same, and to a novel UV-ray absorber and an external skin treatment agent.

More specifically, the present invention relates to a novel silicone type cinnamic acid derivative which can be dissolved in silicone oil, has an excellent water resistance and oil resistance, and has an UV-ray absorbing characteristic at wavelengths in the UV-B region, and to a novel external treatment agent having an excellent sunburn-prevention effect, useability, and prolonged cosmetic effects.

2. Description of the Related Art

As is well known, UV-rays cause various changes to the skin, and dermatologically, the acting wavelengths thereof are classified into long wavelength UV-rays of 400 to 320 nm, medium wavelength UV-rays of 320 to 290 nm, and short wavelength UV-rays shorter than 290 nm; called UV-A, UV-B, and UV-C, respectively.

Generally, most of the UV-rays to which humans are exposed are sunlight rays, and consist of UV-rays reaching the earth, i.e., UV-A and UV-B, and UV-rays absorbed in the ozone layer and not reaching the earth, i.e., UV-C. Of the UV-rays reaching the earth, UV-B rays cause erythema or blistering when irradiated on the skin at a certain dose or higher, and further, promote the forming of melamine in the skin, i.e., cause a darkening or dyeing of the skin.

Accordingly, protection of the skin from UV-B rays is very important from the viewpoint of preventing an accelerated aging of the skin and a generation or increase of splotching or freckling of the skin, and thus various UV-B absorbers to be used for this purpose have been developed.

Among existing UV-B absorbers, there are known PABA derivatives, cinnamic acid derivatives, salicylic acid derivatives, camphor derivatives, urocannic acid derivatives, benzophenone derivatives, and heterocyclic derivatives, and these UV-B absorbers are utilized exclusively by formulation in external treatment agents such as cosmetics and quasi-drugs.

As the external agent bases, silicone type bases with low molecular weights, such as dimethylpolysiloxane, are widely used, as is well known in the art, due to the excellent useability characteristics of such silicone type bases, e.g., a good extendability, plain feeling, and no stickiness, and an excellent function thereof in that they are not easily removed by sweat or water.

On the other hand, since sun-protection cosmetics in which UV-ray absorbers are formulated are used during hot summer, they are liable to be removed by excessive sweating or skin fat extrusions, and when these products are used at the beach or at a swimming pool, a problem arises in that they are removed when the skin is immersed in water. Therefore, there is obviously a need to enhance the cosmetic durability of these cosmetics, and accordingly, a silicone type base with a low molecular weight such as dimethylpolysiloxane, etc., is now widely used as the external treatment agent base, due in the most part to the properties possessed by silicone type bases; for example, a useability such as good spreadability, a plain feeling, no stickiness, and further, functional characteristics such as an excellent water resistance, oil resistance, and resistance to easy removal by sweat or water.

Nevertheless, existing UV-B absorbers have a remarkably low compatibility with or low solubility in silicone type bases, and accordingly, to formulate such UV-B absorbers in an external treatment agent having a silicone type base, an oily base must be added, and therefore, a drawback arises in that the useful properties of the silicon type base as described above are lost, and further, these compositions have an inferior water resistance and oil resistance.

Japanese Examined Patent Publication (Kokoku) No. 29866/1969, Japanese Unexamined patent Publications (Kokai) Nos. 58991/1985 and 108431/1985 disclose compositions having a UV-ray absorbability, but the chemical structures thereof include unsubstituted cinnamic acid as the basic skeleton, which has an absorption maximum wavelength on the UV-C side, in silicone oil, and thus the UV-B absorbability thereof is not satisfactory. FIG. 3 shows the UV absorption spectrum of 3-bis(trimethysiloxy)-methylsilyl-2-methylpropyl-cinnamate, from which it can be understood that this composition does not have an adequate wavelength region for a UV-B absorber.

SUMMARY OF THE INVENTION

Accordingly, the objects of the present invention are to eliminate the above-mentioned disadvantages of the prior art and to develop a UV-ray absorber which can be dissolved in silicone oil, has an excellent water resistance and oil resistance, and can provide a satisfactory absorbing properties of UV-rays having wavelengths in the UV-B region.

Another object of the present invention is to provide a novel silicone type cinnamic acid derivative which can be dissolved in silicone oil, has an excellent water resistance and oil resistance, and has an adequate UV-B wavelength blocking region.

A further object of the present invention is to provide a method of preparing the above-mentioned silicone type cinnamic acid derivative at a high conversion.

A further object of the present invention is to provide an external treatment agent having an excellent UV-B absorbing effect and having a UV-B absorber stably formulated thereinto.

A still further object of the present invention is to provide an external treatment agent having an excellent useability or applicability and providing an excellent UV-B absorbing effect.

Other objects and advantages of the present invention will be apparent from the following description.

In accordance with the present invention, there is provided a silicone type cinnamic acid derivative which is a siloxane having at least one unit represented by the formula (I):

$$\underset{O_{(3-n)/2}S_{i}-R^{2}-O-C-CH=CH-\langle\bigcirc\rangle-X_{a}}{\overset{R^{1}_{n}}{\mid}}\quad\overset{O}{\overset{\|}{C}}\quad\text{(I)}$$

and having the other units which can exist in said siloxane being represented by the formula $O_{(4-m)/2}SiR^3m$ wherein $R^1$ represents an alkyl group having 1 to 4 carbon atoms, a phenyl group, or a trimethylsiloxy group, $R^2$ is a divalent hydrocarbon group having at least two carbon atoms, which may include a heteroatom O, X is an alkoxy group, n is an integer of 0 to 3, a, is an integer of 2 or 3, $R^3$ is an alkyl group having 1 to 4 carbon atoms, a phenyl group, or trimethylsiloxy group, and m is an integer of 0 to 3.

In accordance with the present invention, there is also provided a method of preparing the above-mentioned silicone type cinnamic acid derivative (I), which comprises reacting a cinnamic acid ester represented by the formula:

$$\underset{Y-OC-CH=CH-\langle\bigcirc\rangle-X_{a}}{\overset{O}{\overset{\|}{}}}\quad\text{(II)}$$

wherein Y represents a monovalent hydrocarbon group having at least two carbon atoms and an olefinic unsaturated bond, which may include a heteroatom O, X is an alkoxy group, and a is 2 or 3, with a siloxane having an $$\underset{R^{1}nSiO_{(3-n)/2}}{\overset{H}{\mid}}\quad\text{(III)}$$

unit and $R^3{}_mSiO_{(4-m)/2}$ unit, wherein $R^1$ and $R^3$ represent an alkyl group having 1 to 4 carbon atoms, a phenyl group, or a trimethylsiloxy group, and n and m are integers of 0 to 3, in an organic solvent in the presence of a catalyst.

In accordance with the present invention, there is further provided a method of preparing a silicone type cinnamic acid derivative (I), comprising the step of reacting a cinnamic acid salt having the formula:

$$X_{a}-\langle\bigcirc\rangle-CH=CH-\underset{\overset{\|}{O}}{C}-OZ\quad\text{(IV)}$$

wherein X represents an alkoxy group, Z represents an alkali metal, and a is 2 or 3, with a halogenoalkylene silicone derivative having the formula:

$$\underset{WR^{2}-SiO_{(3-n)/2}}{\overset{R_{n}^{1}}{\mid}}\quad\text{(V)}$$

wherein W represents a halogen, $R^1$ represents an alkyl group having 1 to 4 carbon atoms, a phenyl group, or a trimethylsiloxy group, $R^2$ is a divalent hydrocarbon group having at least two carbon atoms, which may include a heteroatom O, and n is an integer of 0 to 3 in an organic solvent.

In accordance with the present inventions, there is further provided a method of preparing a silicone type cinnamic acid derivative (I), comprising the step of reacting a cinnamic acid ester (II) with a siloxane (III) in the presence of a platinum vinyl siloxane catalyst in an organic solvent.

In accordance with the present invention, there is further provided a UV-ray absorber comprising the above-mentioned silicone type cinnamic acid derivative (I).

In accordance with the present invention, there is still further provided an external treatment agent comprising the above-mentioned silicone type cinnamic acid derivative (I).

BRIEF DESCRIPTION OF THE DRAWINGS

The present invention will be better understood from the description set forth below with reference to the accompanying drawings, in which.

DESCRIPTION OF THE PREFERRED EMBODIMENTS

Figure 1:
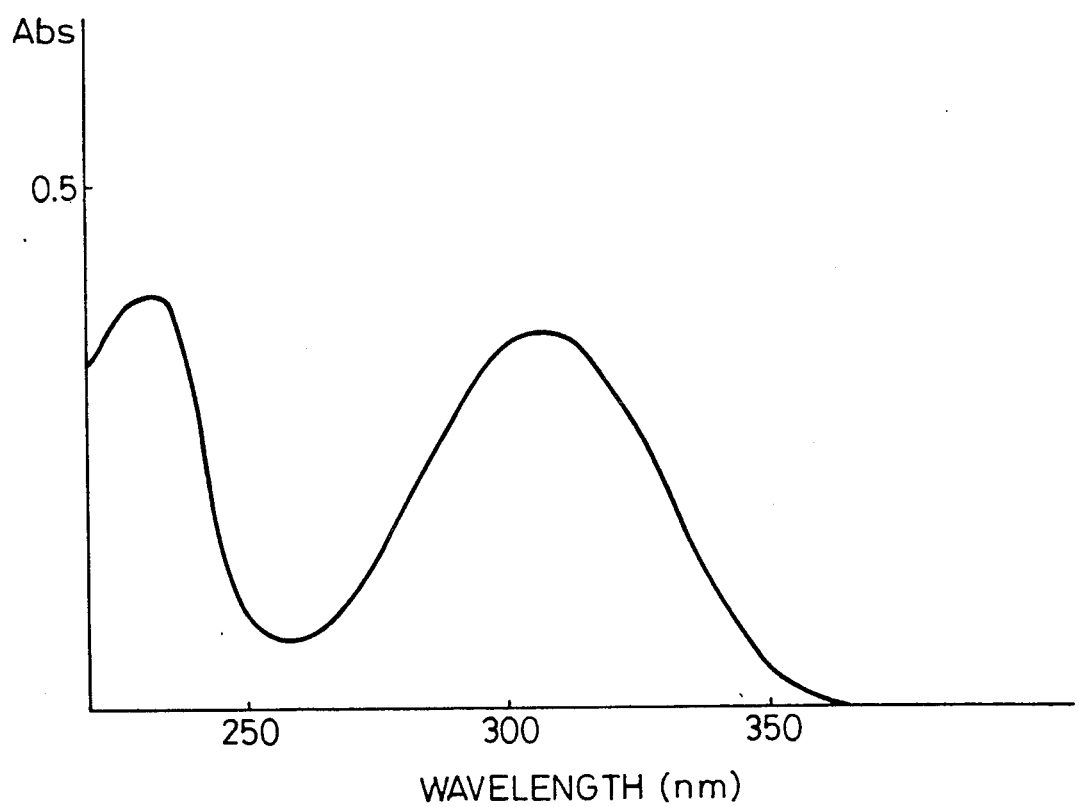
FIG. 1 shows a UV-spectrum of the silicone type cinnamic derivative obtained in Synthesis Example 2 at a concentration of 10 ppm (solvent, ethanol)

The present invention is now described in detail.

The silicone type cinnamic acid derivative is constituted by the unit represent by the formula (I) and the formula $O_{4-m)/2}SiR^3m$. Examples of $R^1$ as defined in the formula include methyl, ethyl, propyl, isopropyl, butyl, isobutyl, t-butyl, phenyl groups, and a trimethylsiloxy group, but preferably a methyl group, a partially phenyl group, or a trimethylsiloxy group is used as the starting materials since they are readily available. Here, n represents the substitution number of $R^1$. Examples of $R^2$ include $$-CH_2CH_2-,\quad -CH_2CH_2CH_2-,\quad \underset{\overset{|}{CH_3}}{-CH_2CHCH_2-},$$

$$\underset{\overset{|}{(CH_3)_2}}{-CCH_2CH_2-},\quad \underset{\overset{|}{CH_3}}{-CH_2CH(CH_2)_2-}\quad \underset{\overset{|}{CH_3}}{-CH_2CH_2CH-},$$

$$-CH_2CH_2CH_2CH_2-,\quad -CH_2CH_2OCH_2CH_2-$$

hexylene, cyclohexylene, and decylene groups, preferably an alkylene group having 2 to 5 carbon atoms, but to ensure a relatively smaller side reaction from a hydrosilylation reaction, $$\underset{\overset{|}{CH_3}}{-CH_2CH_2CH-},\quad \underset{\overset{|}{CH_3}}{-CH_2CH(CH_2)_2-}$$

is particularly preferred.

Examples of X include an methoxy group, ethoxy group, isopropoxy group and the like. Although these are not remarkably different with regard to a solubility thereof in silicone type bases and in UV-B absorption wavelength, from the aspect of availability or reagents, the methoxy group is particularly preferred. Here, a represents the substitution number of X.

In the siloxane unit represented by the formula $O_{(4-m)/2}SiR^3m$, $R^3$ may include methyl, ethyl, propyl, isopropyl, butyl, isobutyl, t-butyl, phenyl groups, and trimethylsiloxy group but preferably a methyl group, partially phenyl group, or trimethylsiloxy group is used, from the aspect of a ready availability thereof as starting materials. Here m is the substitution number of $R^3$.

The silicone type cinnamic acid derivative of the present invention can be synthesized according to the preparation method of the present invention.

The ester of the formula (II) is obtained by converting the corresponding substituted cinnamic acid in a conventional manner into acid chloride and then reacting it with a monohydric alcohol having an olefinic unsaturated bond in the presence of an amine. As the reaction solvent, conventional organic solvents can be used, but aromatic organic solvents such as toluene, benzene, and xylene are preferred, and preferably the reaction is carried out at a high temperature, more preferably a reflux temperature.

Depending on the alcohol to be used for the reaction, Y in the formula (II) is different but is a monovalent hydrocarbon group having at least two carbon atoms and an oefinic unsaturated bond, which may include a heteroatom O, and includes for example, straight hydrocarbon groups such as $CH_2=CH$, $CH_2=CHCH_2-$, $CH_2=CHCH_2CH_2-$, $CH_2=CH-CH_2CH_2CH_2-$, and $CH_2=CH-CH_2-O-CH_2CH_2-$; branched hydrocarbon groups such as $CH_2=CH-CH(Me)-$, $CH_2=CH-C(Me)_2-$, $CH_2=C(Me)-(CH_2)_2-$, $CH_2=CH-CH(Et)-$, $CH_2=CHC(Et)_2-$, $CH_2=CHCH_2CH(Me)-$, $CH_2=CHCH(Me)-CH_2$, and $CH_2=C(Me)CH_2-$ and having a double bond at the terminal end, and those having an internal double bond such as $MeCH=CH-$, $MeCH=CHCH_2-$, $(Me)_2C=CH-$, $(Me)_2C=CHCH_2-$, $MeCH=CHCH_2-$, and $MeCH_2CH=CH-$ and those having two double bonds such as $CH_2=CH-CH=CH_2-$, $CH_2=C(Me)CH=CH_2-$, and $MeCH=CH-CH=CH_2-$, but an ester having one double bond at the terminal end is desirable from the viewpoint of the superior esterification reaction, hydrosilylation reaction, and stability of the silicone type cinnamic acid derivative derived from these esters (including light stability).

The silicone type cinnamic acid derivative of the present invention is obtained by allowing the ester of the formula (II) thus obtained to undergo a hydrosilylation reaction with siloxane. The siloxane to be used is an organic silicon compound having at least one Si-H, which is represented as the siloxane having an $$\overset{H}{\underset{|}{R_n^1SiO_{(3-n)/2}}}$$

unit and $R_m{}^3SiO_{(4"m)/2}$ unit, for example, (ClEtO)SiH, $(Me_3SiO)_2MeSiH$, $(Me_3SiO)_3SiH$, $(Me_3SiO)MePhSiH$, $(Me_3OSi)EtMeSiH$, $(Me_3OSi)EtPhSiH$, and $H(Me)_2SiOSi(Me)_2OSi(Me)_2H$ but from the aspect of a superior hydrosilylation reaction, ready availability of the silane and siloxane, and solubility in silicone type bases, 1,1,1,3,5,5,5-heptamethyltrisiloxane is preferred. Note, this is not limitative of the present invention, and similar compositions may be used provided that the silicone type cinnamic derivative of the present invention can be prepared without hindrance.

As the reaction solvent, conventional solvents can be used, preferably aromatic organic solvents such as toluene, benzene, and xylene, and preferably the reaction can be carried out at high temperature, more preferably at a reflux temperature. As the catalyst for hydrosilylation, a rhodium complex (Wilkinson complex), ruthenium comple, platinum complex, and chloroplatinate generally well known in the art can be used, but in view of the ready availability of the catalyst and of the simplicity of the operation of the synthetic reaction, a chloroplatinate catalyst is preferred. According to the preferred embodiment of the present invention, a platinum vinyl siloxane catalyst having a formula of $Pt\{[(CH_2=CH)SiMe_2]_2O\}_2$ is used, whereby a very high convention (e.g., almost 100%) can be attained and the desired compound can be obtained at a high yield with a small amount of by-products.

The silicone type cinnamic acid derivative of the present invention can be provided with from low to high molecular weights by selecting the ester of the formula (II) and the above siloxane depending on the purpose, including the properties of changing a liquid to a resinous solid at room temperature.

The silicone type cinnamic acid derivative of the present invention can also be synthesized according to the preparation method of the present invention.

The cinnamic acid salt of the formula (IV) is obtained by reacting the corresponding substituted cinnamic acid with an alkali metal hydroxide in an aqueous or alcoholic solution. The preferable alkali metal is sodium or potassium. Then, the salt (IV) is dried and is reacted with the halogenoalkylene silicone derivative of the formula (V) is an organic solvent (e.g., dimethyl-formamide, dimethylsulfoxide) at an elevated temperature, preferably at 120° C. The preferable halogen is chlorine.

The fields of application of the UV-ray absorber according to the present invention, regardless of the development history described above, are not particularly limited and it can be utilized for various articles in which UV-ray absorbers are incorporated, depending on the characteristics and the purpose of the silicone type cinnamic acid derivative according to the present invention.

The amount when formulated for external treatment agents such as cosmetics and quasi-drugs may depend on the dosage, but preferably is 0.1 to 20% by weight, more preferably 0.5 to 10% by weight.

Any base can be used in the present invention, provided that silicone type cinnamic acid derivatives can be dissolved therein, but particularly when a silicone type base is used, effects such as a good spreadability, plain feeling, no stickiness, etc., and functions such as an excellent water resistance, oil resistance and a resistance to removal by sweat or water, can be obtained.

The silicone type base to be used in the present invention is not particularly limited, and includes, for example, chain polysiloxanes such as dimethylpolysiloxane, methylpolysiloxane, and methylhydrogenpolysiloxane; cyclic polysiloxanes such as decamethylpolysiloxane, dodecamethyl-polysiloxane, and tetramethyltetrahydrogenpolysiloxane; and polyether, fatty acid-modified polysiloxanes, higher alcohol modified polysiloxanes, and amino-modified polysiloxanes.

The dermatological external treatment agent of the present invention can also formulate other components conventionally used in cosmetics and quasi-drugs, such as oil components, lubricants, UV-ray absorbers other than those of the present invention, antioxidants, surfactants, preservatives, perfumes, water, alcohols, and thickeners, if desired.

The fields of application of the dermatological external treatment agent of the present invention are not limited, and it can be utilized for cosmetics and quasi-drugs, depending on the characteristics and the purpose of the silicone type cinnamic acid derivative to be used in the present invention.

Here, any dosage form of the dermatological external treatment agent of the present invention may be used, for example, a powder, cream, paste, stick, liquid, spray, foundation may be utilized, and it may be also emulsified by an emulsifier to produce a W/O or O/W emulsion.

The amount thereof to be formulated may differ depending on the dosage form, as mentioned above, but is generally 0.1 to 20% by weight, preferably 0.5 to 10% by weight.

EXAMPLES

The present invention will now be further illustrated by, but is by no means limited to, the following Examples, wherein all parts and percentages are expressed on a weight basis unless otherwise noted.

Synthesis Examples

The present invention is described in more detail with reference to synthesis examples of the novel silicone type cinnamic derivative of the present invention and the physicochemical properties thereof.

Synthesis Example 1

An amount of 11.94 g of 3,4,5-trimethoxycinnamic acid and 11 ml of thionyl chloride were stirred in 80 ml of benzene at reflux temperature for 3 hours, to be converted to acid chloride, and after removal of the solvent, 80 ml of toluene containing 7.20 g of 1-butene-3-ol was added, followed by cooling the reaction system in an ice bath. Then 40 ml of toluene containing 5.25 g of triethylamine was slowly added and the mixture was stirred for one hour, followed by stirring the mixture at room temperature for one day. After filtration, the toluene layer was washed with water, and after removal of the water, subjected to silica gel column chromatography, using toluene as the solvent, to obtain 10.93 g (74.6%) of 3,4,5-trimethoxycinnamic acid ester.

GC-MS M+292
NMR(CDCl$_3$)7.60(1H, d(J=15.77 Hz)), 6.36(1H, d(J=16.14 Hz)), 6.74(2H, s), 5.92(1H, m), 5.49(1H, m), 5.29(1H, d(J=17.60 Hz)), 5.15(1H, d(J=10.64Hz)), 3.85(9H, s), 1.38(3H, d(J=6.60 Hz)).

Synthesis Example 2

The ester obtained in Synthesis Example 1 (2.9319 g) and 2.2270 g of siloxane (1,1,1,3,5,5,5-heptamethylsiloxane, hereinafter abbreviated as MHM) were poured into 50 ml of toluene, and 2 or 3 drops of 0.1 M chloroplatinate isopropyl alcoholic solution were added, followed by stirring at reflux temperature for 5 hours to carry out the hydrosilylation reaction. The product was isolated by silica gel column chromatography, using toluene as the solvent, to obtain 3.0880 g (59.8%) of an oily silicone type cinnamic acid derivative of the present invention. This product was identified by the following analytical values.

Name of substance:
[3-bis(trimethylsiloxy)methylsilyl-1-methylpropyl]3,4,5-trimethoxycinnamate

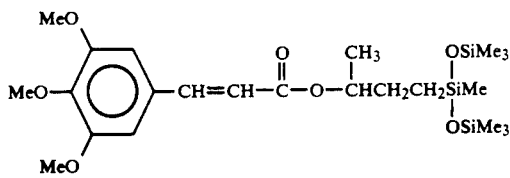

GC-MS M+514
NMR(CDCl$_3$) 7.59(1H, d(J=16.13 Hz)), 6.35(1H, d(J=15.77 Hz)), 6.75(2H, s), 4.95(1H, q), 3.86(9H, s), 1.65(2H, m), 1.29(3H, d(J=6.23 Hz)) 0.54(2H, m), 0.11(18H, s), 0.09(3H, s).

FIG. 1 shows the UV-spectrum at a concentration of 10 ppm (solvent, ethanol), and it was confirmed that the silicone type cinnamic acid derivative, which is the novel compound of the present invention, has a satisfactory absorption in the UV-B wavelength region.

Synthesis Example 3

A hydrosilylation reaction was carried out in the same manner as in Synthesis Example 2 except that benzene was used as the solvent. Then purification was conducted in the same manner to obtain 3.1570 g (61.1%) of the product.

Synthesis Example 4

A hydrosilylation reaction was carried out in the same manner as in Synthesis Example 2, except that xylene was used as the solvent. Then purification was conducted in the same manner to obtain 3.5240 g (68.2%) of the product.

Synthesis Example 5

An amount of 10.48 of 3,4-dimethoxycinnamic acid and 11 ml of thionyl chloride were stirred in 200 ml of benzene at reflux temperature for 2 hours to be converted to acid chloride, and after the solvent was removed, 80 ml of toluene containing 3.63 g of 1-butene-3-ol was added, followed by cooling the reaction system in an ice bath. Then 40 ml of toluene containing 5.10 g of triethylamine was slowly added and the mixture was stirred for one hour, followed by stirring the mixture at room temperature for one day. After filtration, the toluene layer was washed with water, and after removal of the water, subjected to silica gel column chromatography, using toluene as the solvent, to obtain 6.886 g (52.2%) of 3,4-dimethoxy-cinnamic acid ester.

GC-MS M+262
NMR(CDCl$_3$) 7.63(1H, d(J=15.62 Hz)), 6.32(1H, d(J=15.62 Hz)), 6.85(1H, d(J=8.30 Hz), 7.05(1H, s), 7.10(1H, d(J=8.30 Hz)), 5.92(1H, m) 5.50 (1H, m), 5.30(1H, d(J=17.09 Hz)) 5.16(1H, d(J=10.75 Hz)), 3.90(6H, s), 1.29(3H, d(J=6.83 Hz)).

Synthesis Example 6

The ester obtained in Synthesis Example 5 (2.6231 g) and 2.2291 g of siloxane (MHM) were poured into 50 ml of toluene, then 2 or 3 drops of 0.1 M chloroplatinate isopropyl alcoholic solution were added, followed by stirring at reflux temperature for 5 hours to carry out the hydrosilylation reaction. The product was isolated by silica gel column chromatography, using toluene as the solvent, to obtain 2.9157 g (60.1%) of an oily silicone type cinnamic acid derivative of the present invention. This product was identified by the following analytical values.

Name of substance:

[3-bis(trimethylsiloxy)methylsilyl-1-methylpropyl]-3,4-dimethoxycinnamate

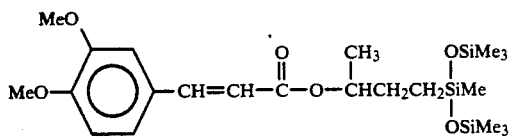

GC-MS M+484
NMR(CDCl$_3$) 7.63(1H, d(J=15.62 Hz)),
6.32(1H, d(J=15.62 Hz)), 6.85(1H,
d(J=8.30 HZ)), 7.05(1H, s),
7.10(1H, d(J=8.30 Hz)), 4.95(1H, q),
3.90(6H, s), 1.65(2H, m), 1.29(3H,
d(J=6.83 Hz)), 0.54(2H, m), 0.11(18H, s),
0.09(3H, s).

Figure 2:
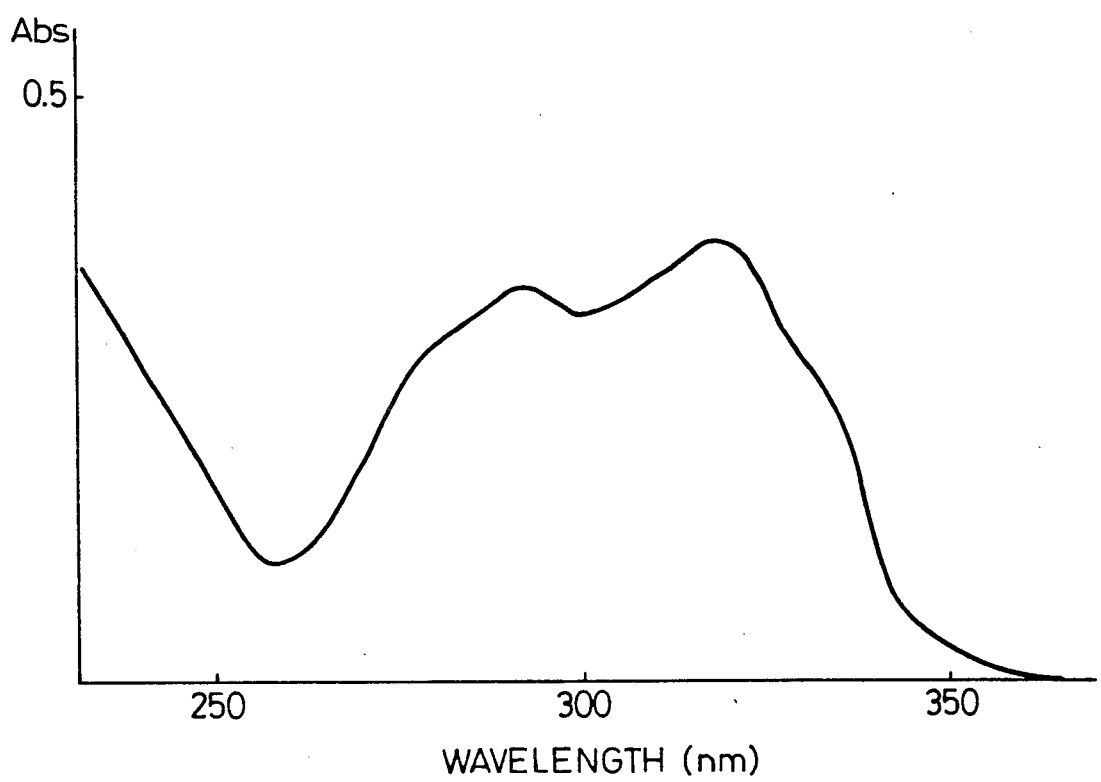
FIG. 2 shows a UV-spectrum of the silicone type cinnamic derivative obtained in Synthesis Example 6 at a concentration of 10 ppm (solvent, ethanol); and, FIG. 3 shows a UV-spectrum of an unsubstituted silicone, which is a known compound, at a concentration of 10 ppm (solvent, ethanol).
Figure 3:
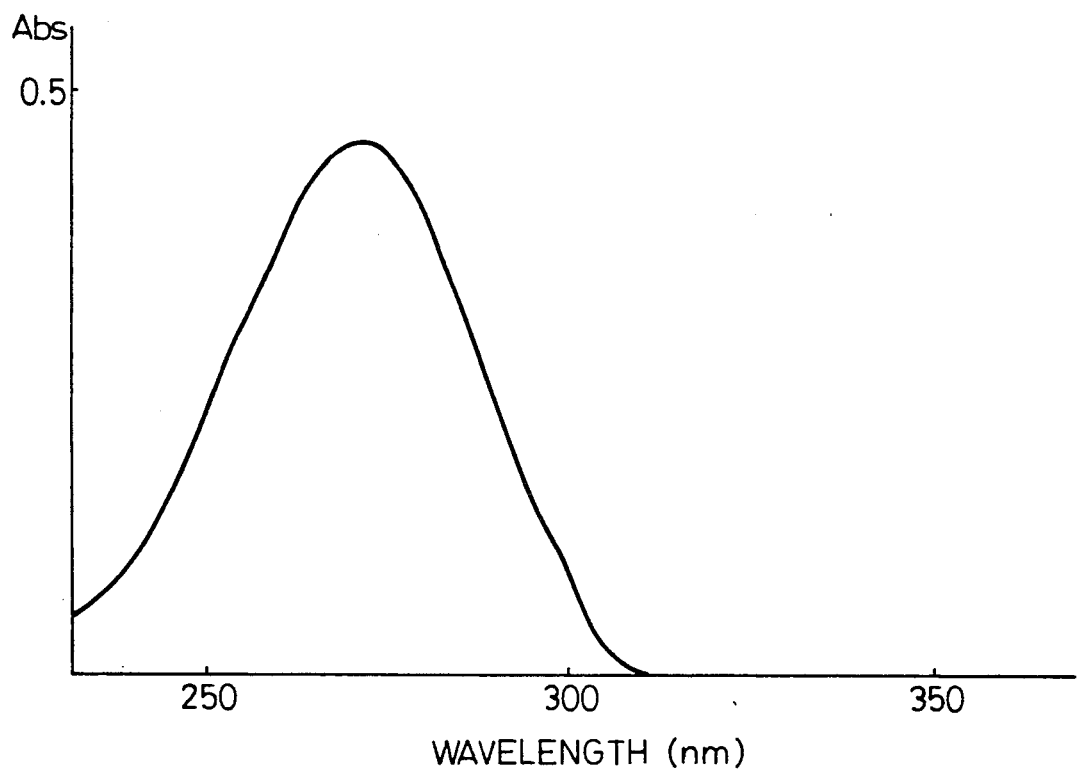

FIG. 2 shows the UV-spectrum at the concentration of 10 ppm (solvent, ethanol), and it was confirmed that the silicone type cinnamic acid derivative, which is the novel compound of the present invention, has a satisfactory absorption in the UV-B wavelength region.

Synthesis Example 7

An amount of 24.1550 g of 3,4,5-trimethoxycinnamic acid and 22 ml of thionyl chloride were stirred in 160 ml of benzene at reflux temperature for 4 hours, to be converted to acid chloride, and after removal of the solvent, 160 ml of toluene containing 5.8550 g of allyl alcohol was added, followed by cooling the reaction system in an ice bath. Then 80 ml of toluene containing 10.111 g of triethylamine was slowly added and the mixture was stirred for 12 hour. After filtration, the toluene layer was washed with water, and after removal of the water, subjected to silica gel column chromatography, using toluene as the solvent, to obtain 20.3039 g (72.0%) of 3,4,5-trimethoxycinnamic acid ester. The product was in the form of a white crystal and the melting point was 67.0°-68.2° C.

GC-MS M+278

Synthesis Example 8

The ester obtained in Synthesis Example 7 (5.6054 g) and 4.4713 g of siloxane (MHM) were poured into 100 ml of benzene, and several drops of H$_2$PtCl$_6$ isopropyl alcoholic solution were added, followed by stirring at reflux temperature for 4 hours to carry out the hydrosilylation reaction. The product was isolated by silica gel column chromatography, using toluene as the solvent, to obtain 2.7846 g (27.6%) of an oily silicone derivative of the present invention. This product was identified by the following analytical values:

[3-bis(trimethylsiloxy)methylsilylpropyl]-3,4,5-trimethoxycinnamate

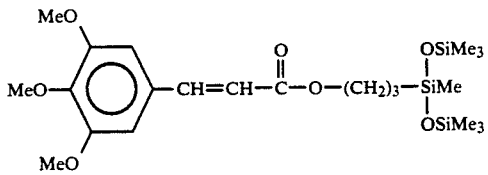

GC-MS M+500
$^1$H-NMR(CDCl$_3$) 7.55(1H, d(J=16.12 Hz)),
6.31(1H, d(J=15.63 Hz)), 6.70(2H, s),
4.11(2H, t), 3.82(9H, s), 1.69(2H, m),
0.51(2H, t), 0.06(18H, s).

The UV-spectrum at a concentration of 10 ppm (solvent, ethanol) of the product was not substantially changed from that (FIG. 1) of the compound of Synthetic Example 2.

Synthesis Example 9

The ester obtained in Synthesis Example 7 (5.000 g) and 5.500 g of siloxane HSi (OSiMe$_3$)$_3$ were poured into 100 ml of benzene, and several drops of H$_2$PtCl$_6$ isopropyl alcoholic solution were added, followed by stirring at reflux temperature for 4 hours to carry out the hydrosilylation reaction. The product was isolated by silica gel column chromatography, using toluene as the solvent, to obtain 2.077 g (20.1%) of an oily silicone derivative of the present invention. This product was identified by the following analytical values.

[3-tris(trimethylsiloxy)silylpropyl]-3,4,5-trimethoxycinnamate

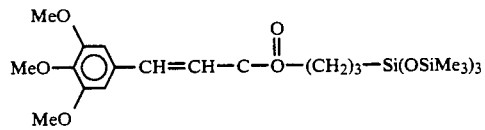

GC-MS M+574
$^1$H-NMR(CDCl$_3$) 7.61(1H, d(J=15.87 Hz)),
6.36(1H, d(J=15.87 Hz)), 6.77(2H, s),
4.17(2H, t), 3.90(9H, s), 1.74(2H, m),
0.53(2H, t), 0.13(18H, s).

The chemical shift was determined by using hydrogen (7.27 ppm) of CDCl$_3$.

The UV-spectrum at a concentration of 10 ppm (solvent, ethanol) of the product was not substantially changed from that of the compound of Synthetic Example 2.

Synthesis Example 10

An amount of 11.960 g of 3,4,5-trimethoxycinnamic acid and 11 ml of thionyl chloride were stirred in 80 ml of benzene at reflux temperature for 3 hours, to be converted to acid chloride, and after removal of the solvent, 80 ml of toluene containing 3.640 g of 1-butene-4-ol was added, followed by cooling the reaction system in an ice bath. Then 40 ml of toluene containing 5.340 g of triethylamine was slowly added and the mixture was stirred for 24 hours, followed by stirring the mixture at room temperature for 24 hours. After filtration, the toluene layer was washed with water, and after removal of the water, subjected to silica gel column chromatography, using toluene as the solvent, to obtain 10.0342 g (68.4%) of 3,4,5-trimethoxycinnamic acid ester. The product was in the form of white crystal having a melting point of 61.8°-63.8° C.

GC-MS M+292

Synthesis Example 11

The ester obtained in Synthesis Example 10 (2.9303 g) and 2.2289 g of siloxane (MHM) were poured into 100 ml of benzene, and several drops of H$_2$PtCl$_6$ isopropyl alcoholic solution were added, followed by stirring at reflux temperature for 2 hours to carry out the hydrosilylation reaction. The product was isolated by silica gel column chromatography, using toluene as the solvent, to obtain 3.1488 g (61.0%) of an oily silicone derivative of the present invention. This product was identified by the following analytical values.

[4-bis(trimethylsiloxy)methylsilylbutyl]-3,4,5-trimethoxycinnamate

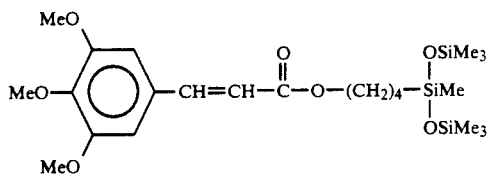

GC-MS M+514
$^1$H-NMR(CDCl$_3$) 7.59(1H, d(J=15.62 Hz)),
6.35(1H, d(J=16.11 Hz)), 6.74(2H, s),
4.21(1H, t), 3.87(9H, s), 1.75(2H, m),
1.47(2H, m), 0.51(2H, m), 0.10(18H, s),
0.01(3H, s).

The UV-spectrum at a concentration of 10 ppm (solvent, ethanol), of the product was not substatially changed form that of the compound obtained in Synthesis Example 2 (FIG. 1)

Synthesis Example 12

A hydrosilylation reaction was carried out in the same manner as in Synthesis Example 11, except that siloxane HSi(OSiMe$_3$)$_3$ was used. By silica gel column chromatography, an oily silicone derivative of the present invention was obtained. This product was identified by the following analytical data.

[4-bis(trimethylsiloxy)silylbutyl]-3,4,5-trimethoxycinnamate

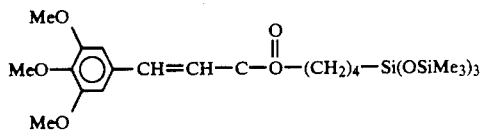

GC-MS M+588
$^1$H-NMR(CDCl$_3$) 7.59(1H, d(J=15.62 Hz)), 6.35(1H, d(J=16.11 Hz)), 6.74(2H, s), 4.21(2H, t), 3.87(9H, s), 1.75(2H, m), 1.47(2H, m), 0.51(2H, m) 0.10(27H, s).

The UV-spectrum at a concentration of 10 ppm (solvent, ethanol), of the product was not substnatially changed form that of the compound obtained in Synthesis Example 2 (FIG. 1)

Synthesis Example 13

A hydrosilylation reaction was carried out in the same manner as in Synthesis Example 6, except that siloxane HSi(OSiMe$_3$)$_3$ was used. By silica gel column chromatography, an oily silicone derivative of the present invention was obtained. This product was identified by the following analytical data.

[3-tris(trimethylsiloxy)silyl-1-methylpropyl]-3,4-dimethoxycinnamate

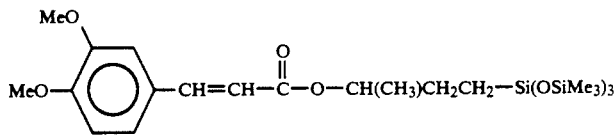

GC-MS M+558
$^1$H-NMR(CDCl$_3$) 7.63(1H, d(J=15.62 Hz)), 6.32(1H, d(J=15.62 Hz)), 6.85(1H, d(J=8.30Hz), 7.05(1H, s), 7.10(1H, d(J=8.30 Hz), 4.95(1H, q),
3.90(6H, s), 1.65(2H, m),
1.29(3H, d(J=6.83 Hz))
0.54(2H, m), 0.10(27H, s).

The UV-spectrum at a concentration of 10 ppm (solvent, ethanol), of the product was not substantially changed form that of the compound obtained in Synthesis Example 6 (FIG. 2)

Synthesis Example 14

An amount of 23.912 g of 3,4,5-trimethoxycinnamic acid and 22 ml of thionyl chloride were stirred in 700 ml of benzene at reflux temperature for 2 hours, to be converted to acid chloride, and after removal of the solvent, 160 ml of toluene containing 10.332 g of ethylene glycol monoallyl ether (CH$_2$=CHCH$_2$OCH$_2$CH$_2$OH), was added, followed by cooling the reaction system in an ice bath. Then 80 ml of toluene containing 10.233 g of triethylamine was slowly added and the mixture was stirred for 24 hours. After filtration, the toluene layer was washed with water, and after removal of the water, subjected to silica gel column chromatography, using toluene as the solvent, to obtain 23.189 g (71.7%) of 3,4,5-trimethoxycinnamic acid ester.

GC-MS: M+322
$^1$H-NMR(CDCl$_3$) 7.62(1H, d(J=15.63 Hz)),
6.39(1H, d(J=16.32 Hz)), 6.76(2H, s), 5.92(1H, m)
5.31(1H, d(17.09 Hz)), 5.21(1H, d(J=10.74 Hz)),
4.37(2H, t), 4.06(2H, d(J=5.37 Hz)), 3.88(9H, s),
3.72(2H, t).

Synthesis Example 15

The ester obtained in Synthesis Example 14 (3.2329 g) and 2.2896 g of siloxane (MHM) were refluxed in 50 ml of toluene for 2 hours to carry out the hydrosilylation reaction by using the catalyst. The product was isolated by silica gel column chromatography to obtain 3.9251 g (71.8%) of an oily silicone derivative of the present invention. This product was identified by the following analytical values.

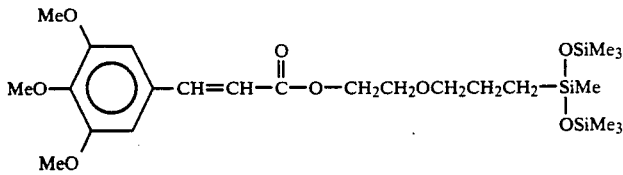

GC-MS M+544

The UV-spectrum at a concentration of 10 ppm (solvent, ethanol) of the product was not substancially changed form that of the compound obtained in Synthesis Example 2 (FIG. 1)

Synthesis Example 16

An amount of 2.613 g of sodium 3,4,5-trimethoxycinnamate was added to toluene and the mixture was stirred under reflux for a while, followed by removing the solvent from the mixture. Thereafter, 100 ml of dimethylformamide was added and 3.015 g of 3-(3-chloropropyl)heptamethyl trisiloxane was gradually added thereto, followed by stirring at 120° C. for 4 hours.

After the reaction was completed, the solvent was removed and the product was isolated by silica gel column chromatorgrapy, using toluene as the solvent, to obtain 3.261 g (65.1%) of an oily silicone derivative of the present invention. The spectrum was identical with that of the derivative obtained by the hydrosilylation.

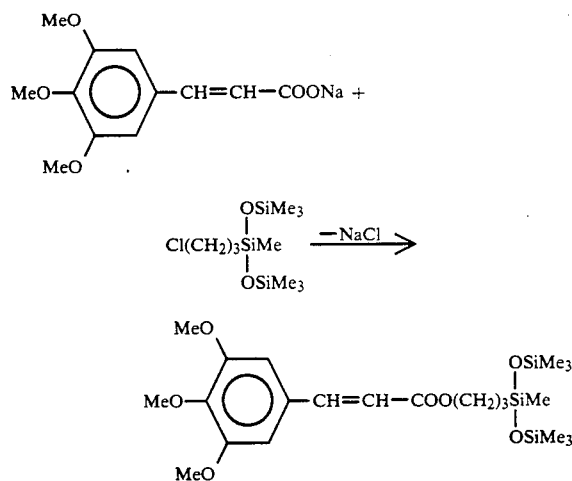

Synthesis Example 17

An amount of 2.625 g of sodium 3,4,5-trimethoxycinnamate was added to toluene and the mixture was stirred under reflux for a while, followed by removing the solvent from the mixture. Thereafter, 100 ml of dimethylformamide was added and 3.732 g of 3-(3-chloropropyl)heptamethyltrisiloxane was gradually added thereto, followed by stirring at 120° C. for 4 hours.

After the reaction was completed, the solvent was removed and the product was isolated by silica gel column chromatograpy, using toluene as the solvent, to obtain 3.432 g (59.7%) of an oily silicone derivative of the present invention. The spectrum was identical with that of the derivative obtained by the hydrosilylation.

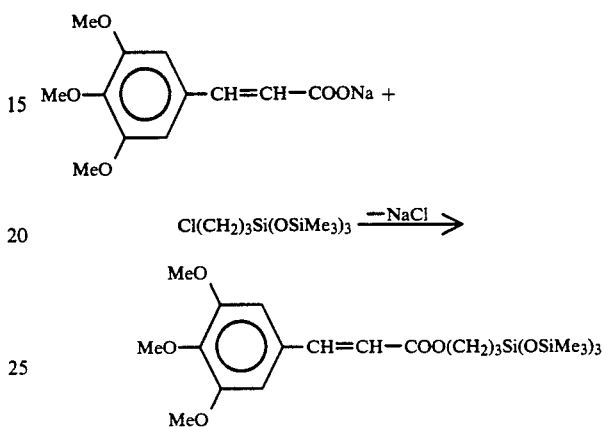

Next, the synthesis of the silicone type cinnamic derivative of the present invention using a platinum vinyl siloxane catalyst and the physicochemical properties are explained below.

First, a platinum vinyl siloxane catalyst was synthesized as follows.

To 5 g amount of a commercially avilable chloroplatinate, 0.6 g of water was added, followed by stirring at room temperature for 2 hours. Thereafter, 50.0 g dimethyl vinylsiloxane (MeViSi)$_2$O was added thereto, followed by stirring at 50°-60° C. for 4 hours. To the reaction system, 5.0 g of NaHCO$_3$ was added, neutralized, and filtered to obtain, a filtrate. Thus, the desired orange platinum vinyl siloxane catalyst Pt{[(CH$_2$=CH)SiMe$_2$]$_2$O}$_2$ was obtained. This synthesis was carried out with reference to the method set forth in Organometallic, 6, 191(1987).

Synthesis Example 18

An amount of 11.94 g of 3,4,5-trimethoxycinnamic acid and 11 ml of thionyl chloride were stirred in 80 ml of benzene at reflux temperature for 3 hours, to be converted to acid chloride, and after removal of the solvent, 80 ml of toluene containing 7.20 g of 1-butene-3-ol was added, followed by cooling the reaction system in an ice bath. Then 40 ml of toluene containing 5.25 g of triethylamine was slowly added and the mixture was stirred for one hour, followed by stirring the mixture at room temperature for one day. After filtration, the toluene layer was washed with water, and after removal of the water, subjected to silica gel column chromatography, using toluene as the solvent, to obtain 10.93 g (74.6%) of 3,4,5-trimethoxycinnamic acid ester.

GC-MS M+292
NMR(CDCl$_3$) 7.60(1H, d(J=15.77 Hz)),
6.36(1H, d(J=16.14 Hz)), 6.74(2H, s),
5.92(1H, m), 5.49(1H, m),
5.29(1H, d(J=17.60 Hz)), 5.15(1H,
d(J=10.64Hz)), 3.85(9H, s),
1.38(3H, d(J=6.60 Hz)).

Synthesis Example 19

A 29.32 g amount of the ester obtained in Synthesis Example 18 and 22.3 g of siloxane (MHM) were poured into ml of toluene, and 0.5 mol% of the platinum vinyl siloxane catalyst was added, followed by stirring at reflux temperature for 5 hours to carry out the hydrosilylation reaction. The product was isolated by silica gel column chromatography, using toluene as the solvent, to obtain 41.50 g (80.5%) of an oily silicone type cinnamic acid derivative of the present invention. This product was identified by the following analytical values.

Name of substance:
[3-bis(trimethylsiloxy)methylsilyl-1-methylpropyl]-3,4,5-trimethoxycinnamate

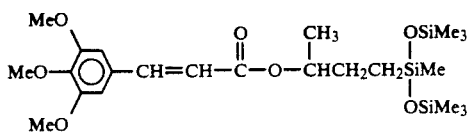

GC-MS M+514
NMR(CDCl$_3$) 7.59(1H, d(J=16.13 Hz)), 6.35(1H, d(J=15.77 Hz)), 6.75(2H, s), 4.95(1H, q), 3.86(9H, s), 1.65(2H, m), 1.29(3H, d(J=6.23 Hz)), 0.54(2H, m), 0.11(18H, s), 0.09(3H, s).

Synthesis Example 20

A hydrosilylation reaction was carried out in the same manner as in Synthesis Example 19 except that benzene was used as the solvent. Then purification was conducted in the same manner to obtain 42.54 g (82.5%) of the product.

Synthesis Example 21

A hydrosilylation reaction was carried out in the same manner as in Synthesis Example 19, except that xylene was used as the solvent. Then purification was conducted in the same manner to obtain 43.97 g (85.3%) of the product.

Synthesis Example 22

An amount of 10.48 of 3,4-dimethoxycinnamic acid and 11 ml of thionyl chloride were stirred in 200 ml of benzene at reflux temperature for 2 hours to be converted to acid chloride, and after the solvent was removed, 80 ml of toluene containing 3.63 g of 1-butene-3-ol was added, followed by cooling the reaction system in an ice bath. Then 40 ml of toluene containing 5.10 g of triethylamine was slowly added and the mixture was stirred for one hour, followed by stirring the mixture at room temperature for one day. After filtration, the toluene layer was washed with water, and after removal of the water, subjected to silica gel column chromatography, using toluene as the solvent, to obtain 6.886 g (52.2%) of 3,4-dimethoxy-cinnamic acid ester.
GC-MS M+262
NMR(CDCl$_3$) 7.63(1H, d(J=15.62 Hz)), 6.32(1H, d(J=15.62 Hz)), 6.85(1H, d(J=8.30 Hz), 7.05(1H, s), 7.10(1H, d(J=8.30 Hz)), 5.92(1H, m) 5.50 (1H, m), 5.30(1H, d(J=17.09 Hz)) 5.16(1H, d(J=10.75 Hz)), 3.90(6H, s), 1.29(3H, d(J=6.83 Hz)).

Synthesis Example 23

An amount of 26.32 g of the ester obtained in Synthesis Example 22 and 22.30 g of siloxane (MHM) were poured into 50 ml of toluene, then 0.5 mol% of the platinum vinyl siloxane catalyst was added, followed by stirring at reflux temperature for 5 hours to carry out the hydrosilylation reaction. The product was isolated by silica gel column chromatography, using toluene as the solvent, to obtain 38.90 g (80.0%) of an oily silicone type cinnamic acid derivative of the present invention. This product was identified by the following analytical values.

Name of substance:
[3-bis(trimethylsiloxy)methylsilyl-1-methylpropyl]-3,4-dimethoxycinnamate

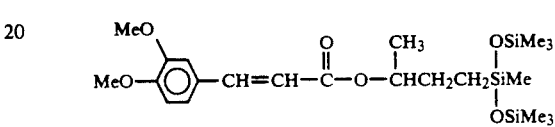

GC-MS M+484
NMR(CDCl$_3$) 7.63(1H, d(J=15.62 Hz)), 6.32(1H, d(J=15.62 Hz)), 6.85(1H, d(J=8.30 HZ)), 7.05(1H, s), 7.10(1H, d(J=8.30 Hz)), 4.95(1H, q), 3.90(6H, s), 1.65(2H, m), 1.29(3H, d(J=6.83 Hz)), 0.54(2H, m), 0.11(18H, s), 0.09(3H, s).

Synthesis Example 24

An amount of 24.1550 g of 3,4,5-trimethoxycinnamic acid and 22 ml of thionyl chloride were stirred in 160 ml of benzene at reflux temperature for 4 hours, to be converted to acid chloride, and after removal of the solvent, 160 ml of toluene containing 5.8550 g of allyl alcohol was added, followed by cooling the reaction system in an ice bath. Then 80 ml of toluene containing 10.111 g of triethylamine was slowly added and the mixture was stirred for 12 hour. After filtration, the toluene layer was washed with water, and after removal of the water, subjected to silica gel column chromatography, using toluene as the solvent, to obtain 20.3039 g (72.0%) of 3,4,5-trimethoxycinnamic acid ester. The product was in the form of a white crystal and the melting point was 67.0°-68.2° C.
GC-MS M+278

Synthesis Example 25

An amount of 56.10 g of the ester obtained in Synthesis Example 24 and 44.80 g of siloxane (MHM) were poured into 100 ml of benzene, and 0.5 mol% of the platinum vinyl siloxane catalyst was stirring at reflux temperature for 2 hours to carry out the hydrosilylation reaction. The product was isolated by silica gel column chromatography, using toluene as the solvent, to obtain 81.95 g (81.2%) of an oily silicone derivative of the present invention. This product was identified by the following analytical values:
[3-bis(trimethylsiloxy)methylsilylpropyl]-3,4,5-trimethoxycinnamate

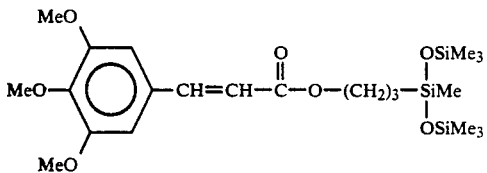

GC-MS M+500
$^1$H-NMR(CDCl$_3$) 7.55(1H, d(J=16.12 Hz)),
6.31(1H, d(J=15.63 Hz)), 6.70(2H, s),
4.11(2H, t), 3.82(9H, s), 1.69(2H, m),
0.51(2H, t), 0.06(18H, s).

Synthesis Example 26

An amount of 50.0 g of the ester obtained in Synthesis Example 24 and 55.0 g of siloxane HSi(OSiMe$_3$)$_3$ were poured into 100 ml of benzene, and 0.5 mol% of the platinum vinyl siloxane catalyst was added, followed by stirring at reflux temperature for 2 hours to carry out the hydrosilylation reaction. The product was isolated by silica gel column chromatography, using toluene as the solvent, to obtain 104.07 g (83.3%) of an oily silicone derivative of the present invention. This product was identified by the following analytical values.

[3-tris(trimethylsiloxy)silylpropyl]-3,4,5-trimethoxycinnamate

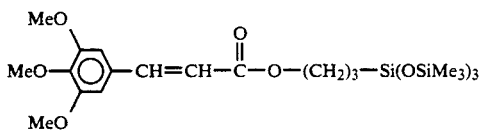

GC-MS M+574
$^1$H-NMR(CDCl$_3$) 7.61(1H, d(J=15.87 Hz)),
6.36(1H, d(J=15.87 Hz)), 6.77(2H, s),
4.17(2H, t), 3.90(9H, s), 1.74(2H, m),
0.53(2H, t), 0.13(18H, s).

Synthesis Example 27

An amount of 11.960 g of 3,4,5-trimethoxycinnamic acid and 11 ml of thionyl chloride were stirred in 80 ml of benzene at reflux temperature for 3 hours, to be converted to acid chloride, and after removal of the solvent, 80 ml of toluene containing 3.640 g of 1-butene-4-ol was added, followed by cooling the reaction system in an ice bath. Then 40 ml of toluene containing 5.340 g of triethylamine was slowly added and the mixture was stirred for 24 hour, followed by stirring the mixture at room temperature for 24 hours. After filtration, the toluene layer was washed with water, and after removal of the water, subjected to silica gel column chromatography, using toluene as the solvent, to obtain 10.0342 g (68.4%) of 3,4,5-trimethoxycinnamic acid ester. The product was in the form of white crystal having a melting point of 61.8°-63.8° C.
GC-MS M+292

Synthesis Example 28

An amount of 29.30 g of an ester obtained in Synthesis Example 27 and 22.29 g of siloxane (MHM) were poured into 100 ml of benzene, and 0.5 mol% of the platinum vinyl siloxane catalyst was added, followed by stirring at reflux temperature for 2 hours to carry out the hydrosilylation reaction. The product was isolated by silica gel column chromatography, using toluene as the solvent, to obtain 41.39 g (80.1%) of an oily silicone derivative of the present invention. This product was identified by the following analytical values.

[4-bis(trimethylsiloxy)methylsilylbutyl]-3,4,5-trimethoxycinnamate

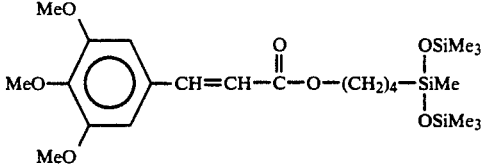

GC-MS M+514
$^1$H-NMR(CDCl$_3$) 7.59(1H, d(J=15.62 Hz)),
6.35(1H, d(J=16.11 Hz)), 6.74(2H, s),
4.21(1H, t), 3.87(9H, s), 1.75(2H, m),
1.47(2H, m), 0.51(2H, m), 0.10(18H, s),
0.01(3H, s).

Synthesis Example 29

A hydrosilylation reaction was carried out in the same manner as in Synthesis Example 28, except that siloxane HSi(OSiMe$_3$)$_3$ was used. By silica gel column chromatography, an oily silicone derivative of the present invention was obtained. This product was identified by the following analytical data. [4-tris(trimethylsiloxy)silylbutyl]-3,4,5-trimethoxycinnamate

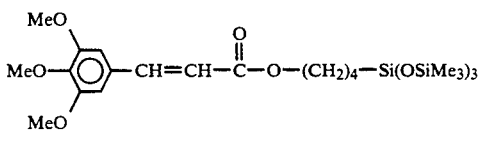

GC-MS M+588
$^1$H-NMR(CDCl$_3$) 7.59(1H, d(J=15.62 Hz)), 6.35(1H, d(J=16.11 Hz)), 6.74(2H, s), 4.21(2H, t), 3.87(9H, s), 1.75(2H, m), 1.47(2H, m), 0.51(2H, m) 0.10(27H,s).

Synthesis Example 30

A hydrosilylation reaction was carried out in the same manner as in Synthesis Example 23, except that siloxane HSi(OSiMe$_3$)$_3$ was used. By silica gel column chromatography, an oily silicone derivative of the present invention was obtained. This product was identified by the following analytical data.

[3-tris(trimethylsiloxy)silyl-1-methylpropyl]-3,4-dimethoxycinnamate

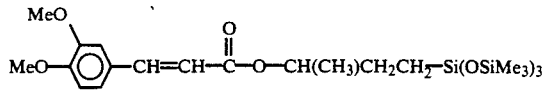

GC-MS M+558
$^1$H-NMR(CDCl$_3$) 7.63(1H, d(J=15.62 Hz)), 6.32(1H, d(J=15.62 Hz)), 6.85(1H, d(J=8.30Hz), 7.05(1H, s), 7.10(1H, d(J=8.30 Hz), 4.95(1H, q), 3.90(6H, s), 1.65(2H, m), 1.29(3H, d(J=6.83 Hz)), 0.54(2H, m), 0.10(27H, s).

Synthesis Example 31

An amount of 23.912 g of 3,4,5-trimethoxycinnamic acid and 22 ml of thionyl chloride were stirred in 700 ml of benzene at reflux temperature for 2 hours, to be converted to acid chloride, and after removal of the solvent, 160 ml of toluene containing 10.332 g of ethylene glycol monoallyl ether (CH₂=CHCH₂OCH₂CH₂OH), was added, followed by cooling the reaction system in an ice bath. Then 80 ml of toluene containing 10.233 g of triethylamine was slowly added and the mixture was stirred for 24 hours. After filtration, the toluene layer was washed with water, and after removal of the water, was subjected to silica gel column chromatography, using toluene as the solvent, to obtain 23.189 g (71.7%) of 3,4,5-trimethoxycinnamic acid ester.
GC-MS: M+322
¹H-NMR(CDCl₃) 7.62(1H, d(J=15.63 Hz)),
6.39(1H, d(J=16.32 Hz)), 6.76(2H, s), 5.92(1H, m)
5.31(1H, d(17.09 Hz)), 5.21(1H, d(J=10.74 Hz)),
4.37(2H, t), 4.06(2H, d(J=5.37 Hz)), 3.88(9H, s),
3.72(2H, t).

Synthesis Example 32

The ester obtained in Synthesis Example 31 (3.2329 g) and 2.2896 g of siloxane (MHM) were refluxed in 50 ml of toluene for 2 hours to carry out the hydrosilylation reaction by using 0.5 mol% of the platinum vinyl siloxane catalyst. The product was isolated by silica gel column chromatography to obtain 4.647 g (85.0%) of an oily silicone derivative of the present invention. This product was identified by the following analytical values.

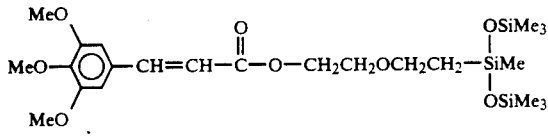

GC-MS M+544

Synthesis Example 33

An amount of 11.96 g of 3,4,5-trimethoxycinnamic acid and 11 ml of thionyl chloride were stirred in 80 ml of toluene at reflux temperature for 3 hours, to be converted to acid chloride, and after removal of the solvent, 80 ml of toluene containing 4.35 g of 3-methyl-3-buten-1-ol was added, followed by cooling the reaction mixture in an ice bath. Then 40 ml of toluene containing 5.34 g of triethylamine was slowly added and the mixture was stirred for 24 hours, followed by stirring the mixture at room temperature for 24 hours. After filtration, the toluene layer was washed with water, and after removal of the water, subjected to silica gel column, chromatography using toluene as the solvent, to obtain 10.63 g (69.1%) of 3,4,5-trimethoxycinnamic acid ester.
GC - MS: M+306

Synthesis Example 34

An amount of 30.71 g of the ester obtained in Synthesis Example 33 and 22.31 g of siloxane (MHM) were dissolved in 100 ml of toluene, then 0.5 mol% of platinum vinyl siloxane catalyst was added, followed by stirring at reflux temperature for 5 hours to carry out the hydrosilylation reaction. The product was isolated by silica gel column chromatography, using toluene as the solvent, to obtain 41.36 g (78.0%) of an oily silicone type cinnamic acid derivative of the present invention. This product was identified by the following analytical values.
Name of substance:
[4-bis(trimethylsiloxy)methylsilyl-3-methylbutyl]-3,4,5-trimethoxycinnamate

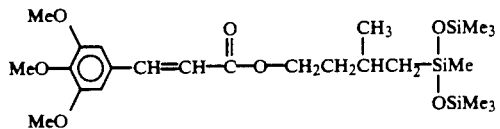

GC - MS M+528
NMR(CDCl₃) 7.59(1H, d(J=15.6Hz))
6.34(1H, d(J=15.6Hz)), 6.77(2H, s),
4.23(2H, t(J=7.0Hz)), 3.88(9H, s),
1.84(1H, m), 1.74(1H, m), 1.58(1H, m)
1.01(3H, d(J=6.8Hz)), 0.62(1H, dd(J=5.4, 14.8Hz))
0.44(1H, dd(J=8.6, 14.8Hz)), 0.10(18H, s),
0.05(3H, s)

To determine the solubilities of the silicone type cinnamic acid derivatives (dimethoxy, trimethoxy substituted derivatives) obtained in Synthesis Examples 2–4, 6, 8, 9, 11–13, and 15, the solubility tests in dimethylpolysiloxane and methylphenylpolysiloxane were conducted at 25° C. In all of the tests, these derivatives were dissolved at 10% by weight or more, thus exhibiting an excellent solubility. Note, the esters obtained as precursors exhibited substantially no solubility.

To test the water resistance and oil resistance thereof, the silicone type cinnamic acid derivatives (dimethoxy, trimethoxy substituted derivatives) of the present invention were mixed, while stirring with water, a 50% ethanolic solution, and oils such as fluid paraffin, and were left to stand at 50° C. for 60 days. No hydrolysis occurred, and thus it was confirmed that these derivatives had an excellent water resistance and oil resistance.

Examples of the use thereof as UV-ray absorbers are shown, and from the UV-spectra shown in FIGS. 1 and 2, it is obvious that these derivatives had a particularly excellent UV-B absorption effect.

The conventional UV-ray absorbers sometimes have properties such that the electron spectra thereof are shifted by, for example, 10 to 20 nm in a base or solvent into which UV-ray absorbers are incorporated. For example, the electron spectrum of N,N-dimethyl 2-ethylhexylcinnamate is shifted by about 10 nm in ethanol and dimethyl polysiloxane. It is required in the art that the solvent dependency of UV-ray absorbers be small. The silicone cinnamic acid derivatives of the present invention advantageously meet the above-mentioned requirements.

Furthermore, UV-ray absorbers are required to provide safety as a UV-ray absorber and a stability against heat and light. The silicone type cinnamic acid derivatives according to the present invention have no problems with the safety of, for example, the contact sensitization, photo-contact sensitization, mutagenicity, and photo-toxicity, and have a good heat stability including hydrolysis. Regarding the light stability, the present cinnamic acid derivatives are stable under normal sunlight irradiation conditions. The photo-isomerization (i.e., trans→cis) occurs only when an ultra-high-pressure mercury lamp is irradiated, but the absorption is still observed in the UV-B region. Thus, the present cinnamic acid derivative is still useful as an excellent UV-ray absorber even after the photo-isomerization. The UV-ray absorption effect when dissolved in a silicon base is shown below.

Example 1: UV-ray absorber (oily type):

| | |
|---|---|
| (1) Decamethylcyclopentasiloxane | 48.0% |
| (2) Dimethylpolysiloxane (10 cs/25° C.) | 20.0% |
| (3) Methylphenylpolysiloxane (20 cs/25° C.) | 20.0% |
| (4) Silicone resin | 10.0% |
| (5) Silicon type cinnamic acid derivative of the present invention | 2.0% |

These components were mixed until dissolved, and then filtered to obtain a product.

Comparative Example 1

A product was obtained in the same way as above, except that (5) was omitted from the recipe of Example 1.

Measurements of the UV-ray prevention effect of Example 1 and Comparative Example 1 obtained as described above were conducted.

The UV-ray prevention effect was measured by using the UV-ray sensitive composition described in Japanese Unexamined Patent Publication (Kokai) No. 62-112020.

The method of preparing the inventive composition is now described.

A solution of 1.0 g of Leuco Crystal Violet, 0.1 g of tetrabromodimethylsulfone, 10 g of an ethylene-vinyl acetate copolymer, and 100 ml of toluene was prepared to provide a Solution I. Separately, a solution of 7 g of N,N-dimethyl-p-aminobenzoic acid-2-ethylhexyl ester, 10 g of an ethylene-vinyl acetate copolymer, and 100 ml of toluene was prepared to provide a Solution II.

The Solution I was coated on an original for photography, and dried to an amount of 1 g/m² as a solid, and then Solution II was coated thereon to an amount of 5 g/m² as a solid, to obtain a UV-ray sensitive composition.

This UV-ray sensitive composition was a paper which changed color from white to pale purple to purple to deep purple in accordance with the increase in the dosage of UV-rays irradiated thereon. An amount of 40 mg of the sample to be measured was mixed with 12 g of castor oil and subjected to the roller treatment to be uniformly dispersed therein. A transparent PET film was placed on the above UV-ray sensitive composition shaped as a circle 5 cm in diameter, and 1.5 g of the composition was coated to a uniform thickness thereon and irradiated by a UV-ray lamp for 8 minutes. Then, the PET film was removed, together with the sample, and the color of the UV-ray sensitive composition was measured by a model 607 Spectrophotometer (Hitachi), and the color difference was calculated according to the LAB system with the color of the UV-ray sensitive composition, with the dosage of UV-rays at zero as the standard. The results are shown below.

| Synthesis Example No | Color difference |
|---|---|
| Example | |
| 2 | 21 |
| 3 | 21 |
| 4 | 21 |
| 6 | 21 |
| 8 | 20 |
| 9 | 21 |
| 11 | 20 |
| 12 | 20 |
| 13 | 22 |
| 15 | 20 |
| Comparative | 58 |
| Example 1 | |

It can be seen that the color differences of the above-mentioned Examples are smaller than that of Comparative Example 1, and thus exhibit a greater UV-ray prevention effect. Namely, it can be seen that an excellent UV-ray prevention effect can be obtained by formulating the silicone type cinnamic acid derivative of the present invention.

Example 2 Suntan proof cosmetic (oily type)

| | |
|---|---|
| (1) Decamethylcyclopentasiloxane | 48.0% |
| (2) Dimethylpolysiloxane (10 CS/25° C.) | 20.0 |
| (3) Methylphenylpolysiloxane (20 CS/25° C.) | 20.0 |
| (4) Silicone resin | 10.0 |
| (5) Silicon type cinnamic acid derivative[1] | 2.0 |

[1]
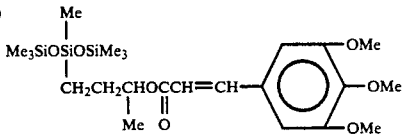

(Preparation method) The components (1) to (5) were mixed and thoroughly dissolved, and then filtered to provide a product.

Comparative Example 2

A product was obtained by using the same procedure as in Example 2, except that the component (5) in the recipe of Example 2 was omitted.

Example 3: Suntan proof cosmetic (W/O cream)

| | |
|---|---|
| (1) Octamethylcyclotetrasiloxane | 28.0% |
| (2) Dimethylpolysiloxane (100 CS/25° C.) | 5.0 |
| (3) Dimethylpolysiloxane (2,500,000 CS/25° C.) | 3.0 |
| (4) Fluid paraffin | 5.0 |
| (5) Silicone type cinnamic acid derivative[2] | 1.5 |
| (6) Polyether-modified silicon (400 CS/25° C.) (polyoxyethylene group content: 20 wt. %) | 6.0 |
| (7) Purified water | 43.1 |
| (8) Sodium L-glutamate | 3.0 |
| (9) 1,3-Butylene glycol | 5.0 |
| (10) Preservative | 0.2 |
| (11) Perfume | 0.2 |

[2]
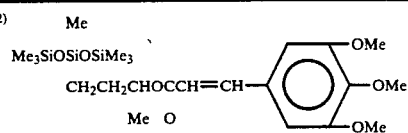

(Preparation method) The components (1) to (6), (11) were mixed, dissolved by heating and maintained at 70° C. to form an oil phase portion, and separately, the components (7) to (10) were dissolved by heating and maintained at 70° C. to form an aqueous phase portion. The aqueous phase portion was added to the oil phase portion, followed by emulsification by an emulsifying machine. After emulsification, the emulsion was cooled while stirring, and when the temperature became 35° C. or lower, the emulsion was cast into a vessel and left to cool and solidify.

Comparative Example 3

A product was obtained by using the same procedure as in Example 3, except that the component (5) in the recipe of Example 3 was omitted.

Example 4 Suntan proof cosmetic (O/W cream)

| | | |
|---|---|---|
| (1) | Decamethylcyclopentacycloxane | 9.0% |
| (2) | Fluid paraffin | 3.0 |
| (3) | Isopropyl myristate | 2.0 |
| (4) | Petrolatum | 5.0 |
| (5) | Cetanol | 5.0 |
| (6) | Stearic acid | 3.0 |
| (7) | Glycerine monoisostearate | 3.0 |
| (8) | Silicone type cinnamic acid derivative[3] | 1.0 |
| (9) | Preservative | 0.2 |
| (10) | Perfume | 0.2 |
| (11) | Glycerin | 10.0 |
| (12) | Propylene glycol | 5.0 |
| (13) | Hyaluronic acid | 0.01 |
| (14) | Potassium hydroxide | 0.2 |
| (15) | Purified water | 53.39 |

[3] 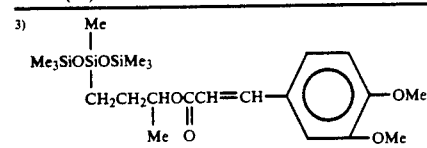

(Preparation method) The components (1) to (10) were heated at 70° C. while stirring to form an oil phase portion, and the components (11) to (15) were completely dissolved by heating at 70° C. to form an aqueous phase portion. The oil phase portion was added to the aqueous phase portion and the mixture was emulsified by an emulsifying machine. The emulsified product was cooled through a heat exchanger to 30° C. and then filled to obtain a product.

Comparative Example 4

A product was obtained by using the same procedure as in Example 4, except that the component (8) in the recipe of Example 4 was omitted.

Example 5: Suntan proof lotion

| | | |
|---|---|---|
| (1) | Dimethylpolysiloxane (5 CS/25° C.) | 10.0% |
| (2) | Methylphenylpolysiloxane (20 CS/25° C.) | 7.0 |
| (3) | Stearic acid | 1.0 |
| (4) | Silicone type cinnamic acid derivative[4] | 10.0 |
| (5) | Preservative | 0.2 |
| (6) | Perfume | 0.2 |
| (7) | Glycerine | 5.0 |
| (8) | Montmorillonite | 0.5 |
| (9) | Potassium hydroxide | 0.2 |
| (10) | Purified water | 65.9 |

[4] 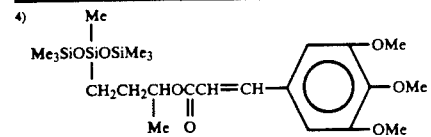

(Preparation method) The components (1) to (6) were heated at 70° C. while stirring to form an oil phase portion, and the components (7) to (10) were dissolved by heating at 70° C. to form an aqueous phase portion. The oil phase portion was added to the aqueous phase portion and the mixture was emulsified by an emulsifying machine. The emulsified product was cooled through a heat exchanger to 30° C. and then filled to obtain a suntan proof lotion.

Comparative Example 5

A product was obtained by using the same procedure as in Example 5, except that the component (4) in the recipe of Example 5 was omitted.

The UV-ray prevention effects of Examples 2 to 5 and Comparative Examples 2 to 5 were then measured by using the UV-ray sensitive composition shown below. The UV-ray prevention effect was measured in the same manner as in comparative Example 1.

The results are shown in Table 1.

TABLE 1

| | Color difference |
|---|---|
| Example 2 | 21 |
| Comparative Example 2 | 58 |
| Example 3 | 32 |
| Comparative Example 3 | 45 |
| Example 4 | 38 |
| Comparative Example 4 | 57 |
| Example 5 | 28 |
| Comparative Example 5 | 52 |

As can be seen from Table 1, the color differences in the Examples are smaller than those in the corresponding Comparative Examples, and thus have a greater UV-ray prevention effect. Therefore, it is clear that a superior UV-ray prevention effect can be obtained by formulating the silicone type cinnamic acid derivative of the present invention.

Example 6: Suntan proof amphibious foundation

| | | |
|---|---|---|
| (1) | Silicon-treated titanium oxide | 9.5% |
| (2) | Silicone-treated mica | 40.0 |
| (3) | Silicone-treated talc | 20.45 |
| (4) | Silicone-treated iron oxide | 7.5 |
| (5) | Spherical nylon powder | 10.0 |
| (6) | Trimethylolpropane triisostearate | 5.0 |
| (7) | Squalane | 3.0 |
| (8) | Beeswax | 2.0 |
| (9) | Silicone type cinnamic acid derivative[5] | 0.5 |
| (10) | Sorbitane trioleate | 1.0 |
| (11) | Preservative | 0.5 |
| (12) | Vitamin E | 0.05 |
| (13) | Perfume | 0.5 |

[5] 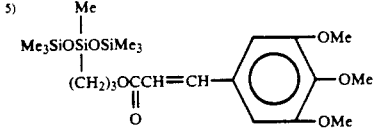

(Preparation method) The components (1) to (5) were mixed by a Henschel mixer and a mixture of the components (6) to (13) were mixed and dissolved by heating and then added thereto and pulverized, followed by molding into a dish to obtain a suntan proof amphibious foundation.

Example 6 was found to have light spreadability, provide a natural finish with a good cosmetic durability, and to have a prolonged UV-ray prevention effect.

Example 7: Suntan proof stick cosmetic

| | | |
|---|---|---|
| (1) | Titanium oxide | 10.0% |
| (2) | Zinc oxide | 7.0 |
| (3) | Mica | 16.0 |
| (4) | Red iron oxide | 1.5 |
| (5) | Yellow iron oxide | 1.5 |
| (6) | Black iron oxide | 1.0 |
| (7) | Dimethylpolysiloxane (20 CS/25° C.) | 29.4 |
| (8) | Trimethylolpropane tri-2-ethylhexanoate | 10.0 |

| | | |
|---|---|---|
| (9) Fluid paraffin | 10.0 | |
| (10) Microcrystalline wax | 2.0 | |
| (11) Ceresin | 1.0 | |
| (12) Solid paraffin | 6.0 | |
| (13) Silicone type cinnamic acid derivative[6] | 3.0 | |
| (14) Perfume | 0.5 | |
| (15) Antioxidant | 0.1 | |
| (16) Sobitane sesquioleate | 1.0 | |

[6] 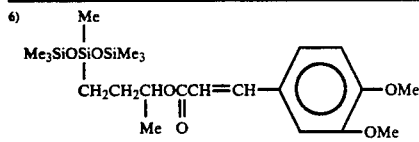

(Preparation method) The components (1) to (6) were mixed by a Henschel mixer, and the mixture was added to the components (7) to (9), (13), (15) and (16), which were dissolved by heating while stirring, and mixed therewith. Next, the melted components of (1) to (12) and (14) were added to the above mixture, and after thoroughly mixing, molded into a stick to obtain a suntan proof stick cosmetic.

Example 7 was found to have a high UV-ray prevention effect and an excellent cosmetic durability.

Example 8: Suntan proof cosmetic base

| | | |
|---|---|---|
| (1) Dimethylpolysiloxane | 19.0% | |
| (2) Glyceryl triisostearate | 10.0 | |
| (3) Isopar (trade mark) G | 5.0 | |
| (4) Sorbitane sesquioleate | 1.0 | |
| (5) Polyoxyalkylene-modified organopolysiloxane | 3.0 | |
| (6) Purified water | 45.0 | |
| (7) 1,3-Butylene glycol | 5.0 | |
| (8) Fine particulate titanium oxide | 10.0 | |
| (9) Silicone type cinnamic acid derivative[7] | 2.0 | |
| (10) Preservative | q.s. | |
| (11) Antioxidant | q.s. | |
| (12) Perfume | q.s. | |

[7] 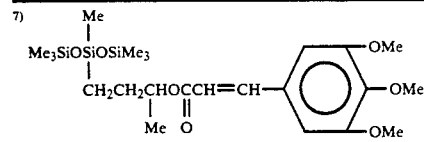

(Preparation method) The components (1) to (5), (9), (11) and (12) were dissolved while stirring, the components (6) to (8) and (10) previously heated to 70° C. were added thereto, and the mixture was emulsified and then cooled to obtain the desired suntan proof cosmetic base.

Example 8 was found to have a high UV-ray prevention effect and an excellent cosmetic durability.

Example 9: Suntan proof stick cosmetic

| | | |
|---|---|---|
| (1) Titanium oxide | 10.0% | |
| (2) Zinc oxide | 7.0 | |
| (3) Mica | 16.0 | |
| (4) Red iron oxide | 1.5 | |
| (5) Yellow iron oxide | 1.5 | |
| (6) Black iron oxide | 1.0 | |
| (7) Dimethylpolysiloxane (20 CS/25° C.) | 29.4 | |
| (8) Trimethylolpropane tri-2-ethylhexanoate | 10.0 | |
| (9) Fluid paraffin | 10.0 | |
| (10) Microcrystalline wax | 2.0 | |
| (11) Ceresin | 1.0 | |
| (12) Solid paraffin | 6.0 | |
| (13) Silicone type cinnamic acid derivative[8] | 3.0 | |
| (14) Perfume | 0.5 | |
| (15) Antioxidant | 0.1 | |
| (16) Sorbitane sesquioleate | 1.0 | |

[8] 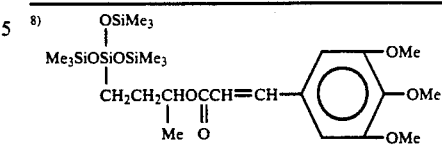

(Preparation method) The components (1) to (6) were mixed by a Henschel mixer, and the mixture was added to the components (7) to (9), (13), (15) and (16) which were dissolved by heating under stirring to be mixed therewith. Next, the melted components of (10) to (12) and (14) were added to the above mixture, and after thorough mixing, molded into a stick to obtain a suntan proof stick cosmetic.

Example 9 was found to have high UV-ray prevention effect and an excellent cosmetic durability, as in Example 7.

Example 10: Suntan proof cosmetic base

| | | |
|---|---|---|
| (1) Dimethylpolysiloxane (2 CS/25° C.) | 19.0% | |
| (2) Glyceryl triisostearate | 10.0 | |
| (3) Isopar (trade mark) G | 5.0 | |
| (4) Sorbitane sesquioleate | 1.0 | |
| (5) Polyoxyethylene-modified organopolysiloxane | 3.0 | |
| (6) Purified water | 45.0 | |
| (7) 1,3-Butylene glycol | 5.0 | |
| (8) Fine particulate titanium oxide | 10.0 | |
| (9) Silicone type cinnamic acid derivative[9] | 2.0 | |
| (10) Preservative | q.s. | |
| (11) Antioxidant | q.s. | |
| (12) Perfume | q.s. | |

[9] 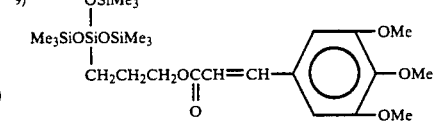

(Preparation method) The components (1) to (5), (9), (11) and (12) were dissolved under stirring, and the components (6) to (8) and (10) previously heated to 70° C. were added thereto and the mixture was emulsified and then cooled to obtain the desired suntan proof cosmetic base.

Example 10 was found to have a high UV-ray prevention effect and an excellent cosmetic durability, as in Example 8.

The silicone type cinnamic acid derivative according to the present invention is an extremely useful substance which absorbs the UV-B wavelength region, exhibits an excellent solubility in silicone oils, and has an excellent water resistance and oil resistance.

The method according to the present invention is extremely efficiently when preparing the compound, and the UV-ray absorber according to the present invention is an excellent UV-ray absorber particularly suitable for external agents such as cosmetics and quasi-drugs. Namely, since this agent can withstand wavelengths in the UV-B region and at the same time, has an excellent solubility in silicone oils, it can be formulated in any desired amount without impairing the characteristics of the silicone type bases, and is a UV-ray absorber having an excellent water resistance and oil resistance.

The dermatological external treatment agent of the present invention can provide a desired protection against the wavelengths in the UV-B region. Also, the UV-B absorber to be used in the present invention has an excellent water resistance and oil resistance, and therefore, can provide a dermatological external treatment agent in which the base and the components to be formulated can be freely selected, and at the same time, has the advantage of an excellent stability even when left to stand under severe conditions, such as in direct sun light. The dermatological external treatment agent of the present invention, which employs a silicone type base, provides a superior useability such as a good spreadability, plain feeling and no stickiness, and a strong resistance to removal by sweat or water (good cosmetic durability), in addition to the above effect. Further, a UV-B absorber can be formulated in any desired amount, and thus another effect is provided in that a dermatological external treatment agent having a widely based UV-ray prevention effect can be obtained.

We claim:

1. A silicone type cinnamic acid derivative which is a siloxane having at least one unit represented by the formula (I):

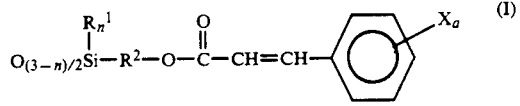

and having other units which can exist in said siloxane being represented by the formula: $O_{(4-m)/2}SiR_m^3$ wherein $R^1$ represents an alkyl group having 1 to 4 carbon atoms, a phenyl group, or a trimethylsiloxy group, $R^2$ is a divalent hydrocarbon group having at least two carbon atoms, which may include a heteroatom O, X is an alkoxy group, n is an integer of 0 to 2, a is an integer of 2 or 3, $R^3$ is an alkyl group having 1 to 4 carbon atoms, a phenyl group, or a trimethyl siloxy group, and m is an integer of 0 to 3, which is prepared by reacting a cinnamic acid ester having the formula:

wherein y represents a monovalent hydrocarbon group having at least two carbon atoms and an olefinic unsaturated bond, which may include a heteroatom O, X is an alkoxy group, and a is 2 or 3 with a siloxane having an

unit and $R_m^3SiO_{(4-m)/2}$ unit in the presence of a platinum vinyl siloxane catalyst in an organic solvent.

2. A method for preparing a silicone type cinnamic acid derivative which is a siloxane having at least one unit represented by the formula (I):

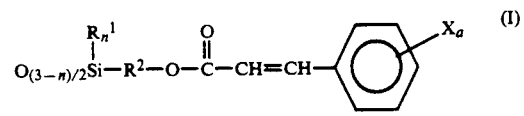

and having other units which can exist in said siloxane being represented by the formula: $O_{(4-m)/2}SiR_m^3$ wherein $R^1$ represents an alkyl group having 1 to 4 carbon atoms, a phenyl group, or a trimethylsiloxy group, $R^2$ is a divalent hydrocarbon group having at least two carbon atoms, which may include a heteroatom O, X is an alkoxy group, n is an integer of 0 to 2, a is an integer of 2 or 3, $R^3$ is an alkyl group having 1 to 4 carbon atoms, a phenyl group, or a trimethylsiloxy group, and m is an integer of 0 to 3, comprising the step of reacting a cinnamic acid ester having the formula:

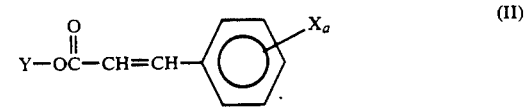

wherein y represents a monovalent hydrocarbon group having at least two carbon atoms and an olefinic unsaturated bond, which may include a heteroatom O, X is an alkoxy group, and a is 2 or 3 with a siloxane having an $$\overset{H}{\underset{R_n^1}{|}}SiO_{(3-n)/2}$$ (III)

unit and $R_m^3SiO_{(4-m)/2}$ unit in the presence of a platinum vinyl siloxane catalyst in an organic solvent.

* * * * *